United States Patent
Dannan

(10) Patent No.: US 10,274,449 B2
(45) Date of Patent: Apr. 30, 2019

(54) CAPACITIVE MOISTURE SENSOR SYSTEM FOR A SURVEILLANCE CAMERA

(71) Applicant: Robert Bosch GmbH, Stuttgart (DE)

(72) Inventor: Benjamin Dannan, Marietta, PA (US)

(73) Assignee: Robert Bosch GmbH, Stuttgart (DE)

( * ) Notice: Subject to any disclaimer, the term of this patent is extended or adjusted under 35 U.S.C. 154(b) by 198 days.

(21) Appl. No.: 15/295,021

(22) Filed: Oct. 17, 2016

(65) Prior Publication Data

US 2018/0106746 A1 Apr. 19, 2018

(51) Int. Cl.
*G01R 27/26* (2006.01)
*G01N 27/22* (2006.01)
*H04N 5/225* (2006.01)

(52) U.S. Cl.
CPC .......... *G01N 27/223* (2013.01); *G01R 27/26* (2013.01); *G01R 27/2605* (2013.01); *H04N 5/2251* (2013.01)

(58) Field of Classification Search
CPC .... G01N 22/00; G01R 27/2605; G01R 27/26; G01D 5/2405; G06F 3/044
USPC .......... 324/76.11–76.83, 459, 600, 634, 640, 324/643, 649, 658, 663, 664, 689
See application file for complete search history.

(56) References Cited

U.S. PATENT DOCUMENTS

| | | |
|---|---|---|
| 4,766,369 A | 8/1988 | Weinstein |
| 5,751,071 A * | 5/1998 | Netzer ............... B60S 1/026 219/203 |
| 5,801,307 A | 9/1998 | Netzer |
| 6,094,981 A | 8/2000 | Hochstein |
| 6,313,454 B1 | 11/2001 | Bos et al. |
| 6,376,824 B1 | 4/2002 | Michenfelder et al. |
| 7,716,981 B2 | 5/2010 | Schmitt et al. |
| 7,772,793 B2 | 8/2010 | Ishikawa |
| 9,040,915 B2 | 5/2015 | Rothenhaeusler et al. |
| 2006/0048572 A1 | 3/2006 | Isogai et al. |
| 2008/0265913 A1 | 10/2008 | Netzer |
| 2009/0085755 A1 | 4/2009 | Schafer et al. |
| 2010/0156846 A1 * | 6/2010 | Long ............... G06F 3/044 345/174 |

(Continued)

FOREIGN PATENT DOCUMENTS

| | | |
|---|---|---|
| EP | 1669779 A1 | 6/2006 |
| EP | 2988122 A1 | 2/2016 |

(Continued)

OTHER PUBLICATIONS

Search Report from the United Kingdom Intellectual Property Office for Application No. GB1717017.6 dated Apr. 17, 2018 (6 pages).

*Primary Examiner* — Huy Q Phan
*Assistant Examiner* — Raul J Rios Russo
(74) *Attorney, Agent, or Firm* — Michael Best & Friedrich LLP

(57) ABSTRACT

An inter-digital capacitive sensor and control system are used to distinguish between rain, ice, dirt and debris on the outer lens surface of a surveillance camera. The electrodes of the capacitive sensor are made from a conductive coating such as printed epoxy or a transparent conductive oxide, that is directly deposited onto the inner surface of the lens. A defroster is spaced radially-outward from the capacitive sensor and is formed by metal deposition directly on the substrate surface.

10 Claims, 8 Drawing Sheets

(56) References Cited

U.S. PATENT DOCUMENTS

| | | | |
|---|---|---|---|
| 2012/0033168 A1* | 2/2012 | Hwang | G02F 1/13338 349/139 |
| 2012/0229882 A1* | 9/2012 | Fish, Jr. | B60R 1/025 359/267 |
| 2013/0019618 A1 | 1/2013 | Veerasamy et al. | |
| 2013/0170013 A1* | 7/2013 | Tonar | B60R 1/088 359/296 |
| 2016/0104024 A1* | 4/2016 | Slogedal | G06K 9/0002 324/649 |
| 2017/0261830 A1* | 9/2017 | Luten | B60R 1/025 |

FOREIGN PATENT DOCUMENTS

| | | |
|---|---|---|
| NL | 2011845 C | 6/2015 |
| WO | 2007081470 A1 | 7/2007 |

* cited by examiner

TRUTH TABLE

| IN1 | IN1 | OUT1 | OUT2 | DESCRIPTION |
|---|---|---|---|---|
| 0 | 0 | HIGH-Z | HIGH-Z | COAST; H-BRIDGE DISABLED TO HIGH-Z (SLEEP ENTERED AFTER 1ms) |
| 0 | 1 | L | H | REVERSE (CURRENT OUT2→OUT1) |
| 1 | 0 | H | L | FORWARD (CURRENT OUT1→OUT2) |
| 1 | 1 | L | L | BRAKE; LOW-SIDE SLOW DECAY |

*FIG. 8B*

CAPACITIVE MOISTURE SENSOR SYSTEM FOR A SURVEILLANCE CAMERA

FIELD

Embodiments of the invention relate to capacitive moisture sensors for surveillance cameras.

BACKGROUND

Surveillance cameras are ubiquitous in many places throughout the world. Many surveillance cameras are located outdoors, and are subject to environmental elements such as rain, ice, snow and dirt. It is important to keep the lenses clear for surveillance cameras so that the images they display or record are readily viewable.

SUMMARY

In one embodiment, the invention provides a capacitive moisture sensor for a surveillance camera having a substrate that may be transparent. The substrate has a first surface configured to being exposed to moisture, and a second surface opposite to the first surface. A first electrode and a second electrode, spaced from the first electrode, are conductively coated on the second surface of the substrate. The first electrode and the second electrode include a transparent conductive material. A first electrical contact and a second electrical contact are deposited on the second surface of the substrate and are connected in circuit with their respective first electrode and second electrode. First and second electrical conductors are connected in circuit to respective first and second electrical contacts.

Another embodiment the invention provides a method of forming a capacitive moisture sensor on a substrate for a camera. The method includes coating a surface of the substrate with a conductive material to form first and second spaced electrodes. First and second electrical contacts are deposited on the substrate, and circuit connections are formed between the first and electrodes and their respective first and second electrical contacts.

Other aspects of the invention will become apparent by consideration of the detailed description and accompanying drawings.

BRIEF DESCRIPTION OF THE DRAWINGS

FIG. 8B is a truth table relating to the H-bridge motor controller depicted in FIG. 8A.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect. Also, electronic communications and notifications may be performed using any known means including direct connections, wireless connections, etc.

It should also be noted that a plurality of hardware and software based devices, as well as a plurality of different structural components may be utilized to implement the invention. It should also be noted that a plurality of hardware and software based devices, as well as a plurality of different structural components may be used to implement the invention. In addition, it should be understood that embodiments of the invention may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software (e.g., stored on non-transitory computer-readable medium) executable by one or more processors. As such, it should be noted that a plurality of hardware and software based devices, as well as a plurality of different structural components may be utilized to implement the invention. For example, "control units" and "controllers" described in the specification can include one or more electronic processors, one or more memory modules including non-transitory computer-readable medium, one or more input/output interfaces, and various connections (e.g., a system bus) connecting the components.

Figure 1:
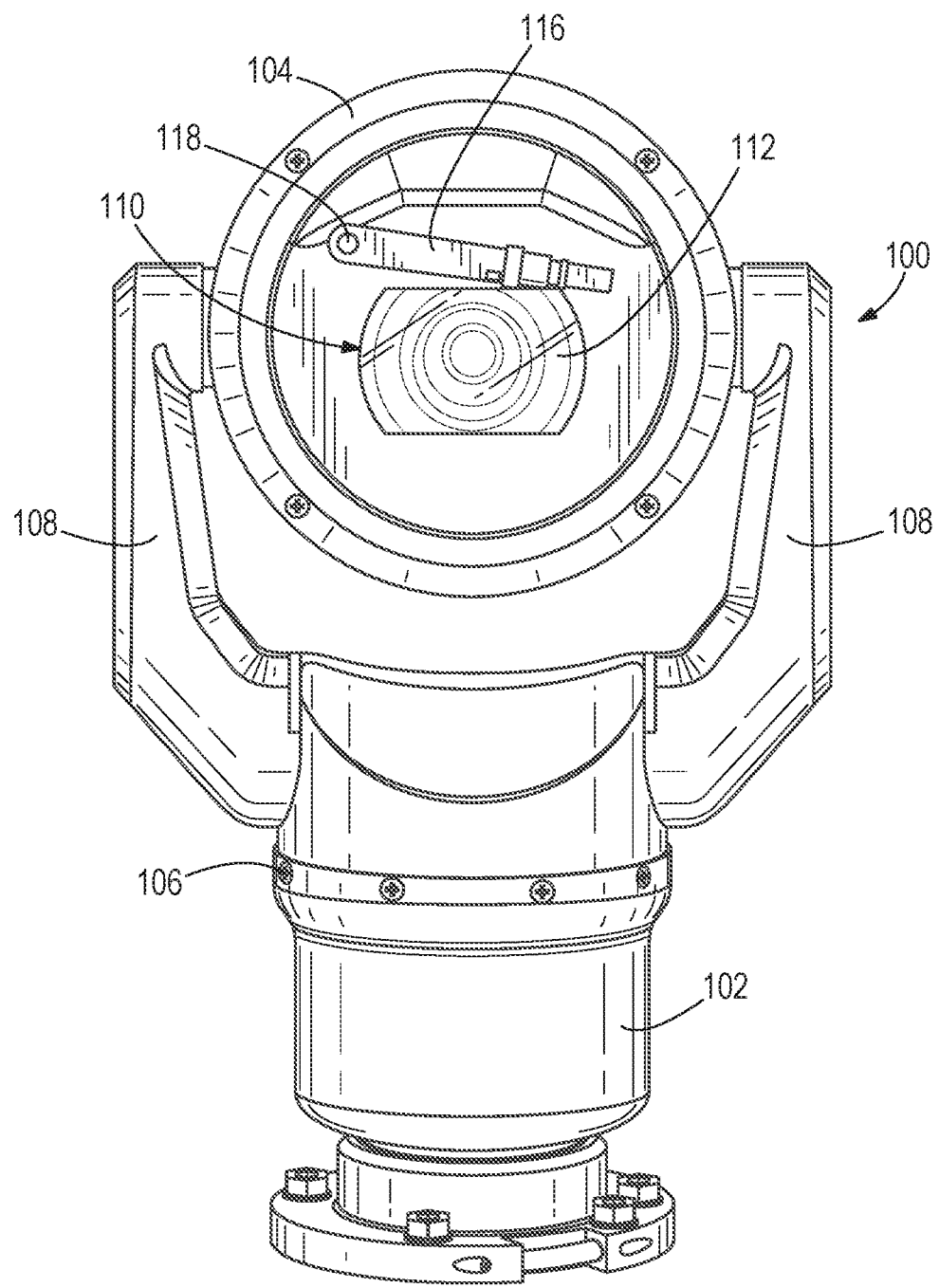
FIG. 1 is a front view of a surveillance camera head incorporating the invention.

FIG. 1 depicts a camera head assembly 100 according to an embodiment of the invention. In FIG. 1, camera head assembly 100 includes a base 102 that is configured to be mounted to a surface. Camera head assembly 100 includes a camera head 104 that can pan its surroundings using swivel mechanism 106. Camera head 104 is also configured to tilt using arms 108.

Figure 2:
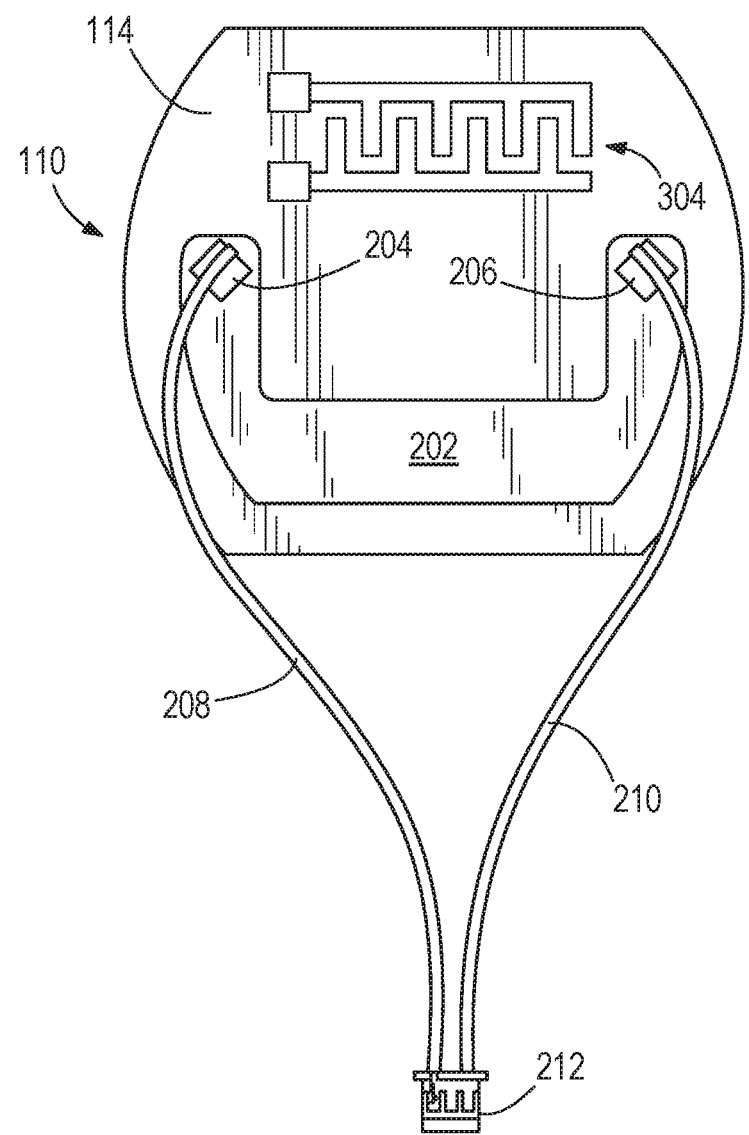
FIG. 2 is a rear view of a camera lens substrate depicting a capacitive moisture sensor and a defroster with electrical contacts and electrical connectors according to the invention.
Figure 5:
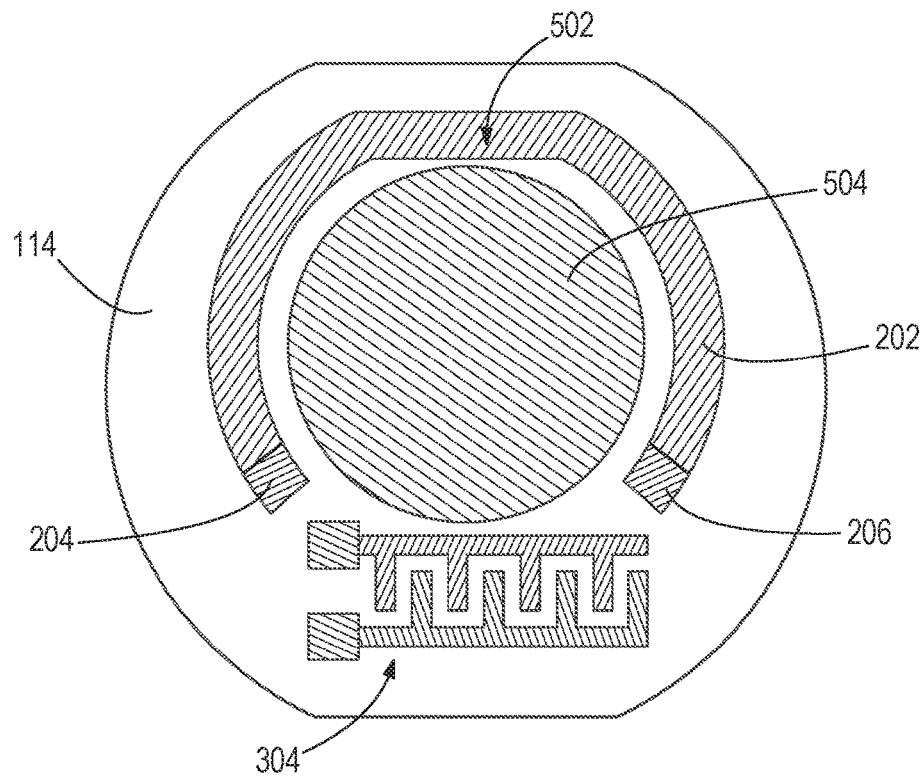
FIG. 5 is a rear view of a camera lens substrate according to one embodiment of the invention.

Referring again to FIG. 1, camera head 104 has a substrate 110 that is the output lens for the camera head 104. Substrate 110 has a first surface 112 configured to being exposed to moisture or other substance, and an opposite second surface 114 (FIGS. 2 and 5). Camera head 104 also has a wiper 116 for cleaning first surface 112 of substrate 110. Wiper 116 pivots at a pivot 118 in response to a reversible DC motor 120 (FIG. 5).

Figure 3:
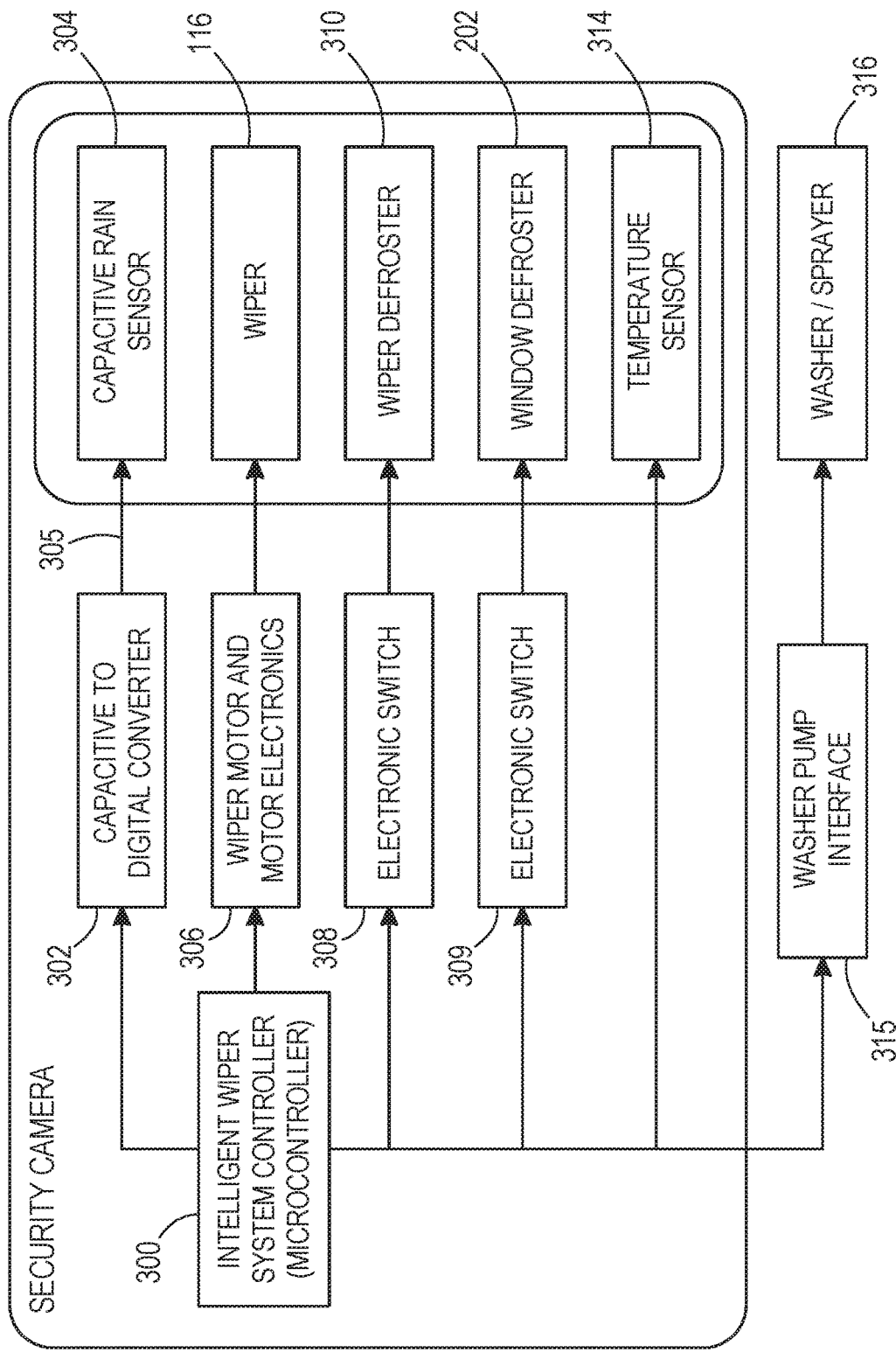
FIG. 3 is a block diagram of a camera sensor system incorporating the invention.

FIG. 2 is a rear view of substrate 110 depicting second surface 114. Substrate 110 may be made of a borosilicate glass such as BOROFLOAT 33 made by Schott Technical Glass Solutions GmbH of Jena, Germany, although other glass compositions may also be suitable. The glass surface is ion pre-cleaned, and then an anti-reflective coating is deposited on second surface 114. A defroster 202 is then deposited on second surface 114 as more fully explained in connection with FIG. 5, and two electrical contacts 204 and 206 are deposited onto defroster 202. Electrical wires 208 and 210 are connected between respective electrical contacts 204 and 206 on the one hand, and connector 212 on the other hand. Connector 212 is connected to a controller 300 (FIG. 3) through a transistor switch 309 (FIGS. 3 and 4). Capacitive moisture sensor 304 is also disposed on second surface 114, as discussed below.

FIG. 3 is a block diagram of a camera moisture sensor system according to an embodiment of the invention. In FIG. 3, controller 300 (FIGS. 3 and 4) communicates with a capacitive to digital converter 302, which in turn communicates with capacitive moisture sensor 304 through an electrical conductor 305. Capacitive moisture sensor 304 is disposed on the inner, sealed second surface 114 of substrate 110. See FIGS. 5 and 6. Controller 300 also communicates with wiper motor control electronics 306 to control wiper 116.

Referring again to FIG. 3, controller 300 controls a switch 308, which in turn controls the power to a wiper defroster 310. Controller 300 controls a switch 309 which in turn controls the power to a window defroster 202. In the embodiment depicted in FIGS. 3 and 4A the capacitive moisture sensor system is a closed loop system which includes a temperature sensor 314 that communicates with controller 300 to regulate power to window defroster 202 and wiper defroster 310. Controller 300 also provides control signals to a washer pump interface 315, when in turn communicates with a lens washer 316 when dirt or other debris is detected on first surface 112. Washer pump interface 315 may be a MIC Alarm/Washer Interface Unit from Bosch Security Systems of Fairport, N.Y.

Figures 4A, 4B:
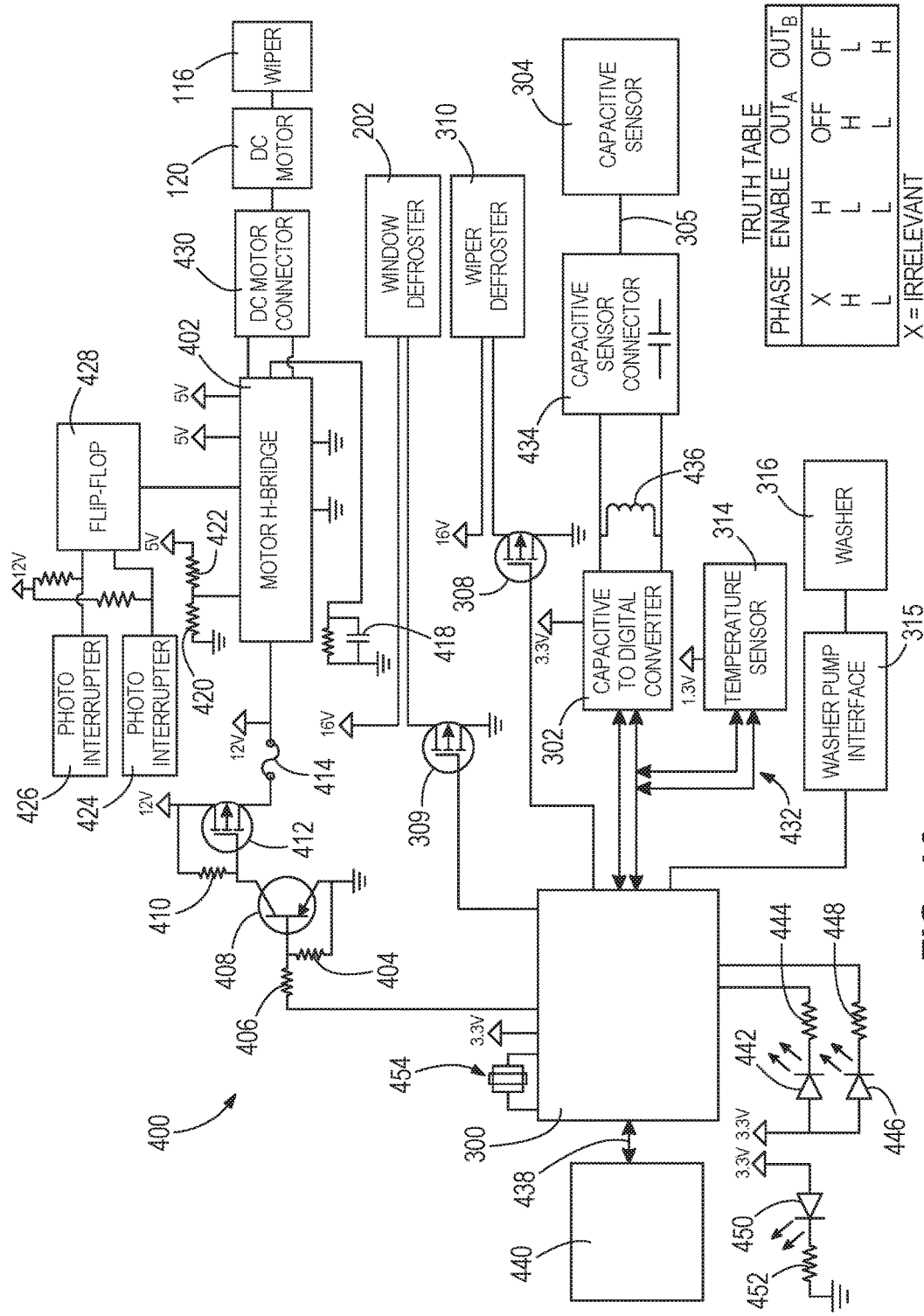
FIG. 4A is a circuit diagram of a capacitive moisture sensor system incorporating the invention.
FIG. 4B is a truth table relating to the phase of the H-bridge wiper motor controller of FIG. 4A.

FIG. 4A is a circuit diagram of a capacitive moisture sensor system according to an embodiment of the invention. In FIG. 4A, circuit 400 includes a controller 300, which may be a STM32F103CBT 32-bit ARM microcontroller with a Cortex M3 CPU core and 128 Kbytes of flash memory, made by STMicroelectronics of Geneva, Switzerland. As discussed above in connection with FIG. 3, controller 300 communicates with the devices and sensors in the capacitive moisture sensor system. In FIG. 4A, an H-bridge 402 controls the DC wiper motor 120. The power supply for H-bridge 402 comprises resistors 404 and 406, and transistor 408 connected in circuit to an output of controller 300. The power supply also includes a resistor 410 connected in circuit with transistor 412 which is connected to the Vbb pin of H-bridge 402 through a fuse 414. H-bridge 402 may be an A3966 dual full-bridge pulse width modulated motor driver made by Allegro of Worcester, Mass. Resistor 416 and capacitor 418 together comprise an RC timing network which sets the fixed-frequency pulse duration of output pulses on outputs Out2a and Out2b of H-bridge 402. A reference voltage is set by resistors 420 and 422, and is applied to pin Vref of H-bridge 402.

The phase or direction of wiper motor 120 is determined by a pair of photo interrupters 424 and 426, which are connected in circuit to a flip-flop 428 and a Phase B pin of H-bridge 402. Each photo interrupter is triggered when it senses the presence of the wiper near the wiper's end of travel, indicating that the current through the DC motor 120, and the direction of the wiper 116, should reverse. The triggered photo interrupter in turn triggers flip-flop 428, which provides either High (H) or Low (L) phase information to pin Phase B.

FIG. 4B is a truth table showing the phase of the output of H-bridge 402 and thus the direction of the wiper motor 120. As shown in FIG. 4B, when the phase is High, motor current flows in a first direction from pin Out2a of H-bridge 402 through the motor connector 430 and motor 120, and returns through pin Out2b of H-bridge 402. When the phase is Low, the current direction and motor reverse, with the current flowing out from pin Out2b through motor connector 430 and motor 120, and returning through pin Out2a.

Referring again to FIG. 4A, controller 300 provides a control signal to a switch 309 to turn ON substrate defroster 202. Similarly, controller 300 provides a control signal to a switch 308 to turn ON a wiper defroster 310. In the closed loop system shown in FIG. 4A, a temperature sensor 314 senses the outer lens or substrate temperature and provides a temperature signal on an inter-integrated circuit bus (I2C1) 432 to controller 300 that enables the controller to determine when to turn ON and OFF the lens defroster 202 and the wiper defroster 310.

The capacitive moisture sensor system shown in FIG. 4A uses a capacitive sensor 304 to determine whether moisture or debris is present on the outer, first surface 112 of substrate 110. In some embodiments, two capacitive sensors 304 are used. Based upon the sensed capacitance, controller 300 determines whether a liquid (e.g. water, black coffee, muddy water), ice or debris is present on the first surface 112 of substrate 110. If a liquid is present on the first surface 112 of the substrate 110, controller 300 communicates with the H-bridge 402 to activate the wiper 116. If controller 300 determines, based upon input from temperature sensor 314, that the substance is frozen, the controller sends control signals to activate the respective switches for the lens and wiper defrosters instead of activating the wiper. If dirt or other debris is sensed, controller 300 activates washer 316 and then activates wiper 116.

As shown in FIG. 4A, the controller communicates with a capacitive to digital converter 302 which converts the signals from capacitive sensor 304 to digital values for input to controller 300. One suitable converter 302 is a FDC 2214 converter made by Texas Instruments of Dallas, Tex. Capacitive sensor 304 is connected in circuit with capacitive to digital converter 302 through a connector 434. An inductor 436 is connected across the two lines between the converter 302 and connector 434. Capacitive sensor 304 is more fully discussed below in connection with FIGS. 5 and 6.

In FIG. 4A, circuit 400 also has a Joint Test Action Group (JTAG) interface 438 connected to a JTAG port of controller 300, and a SUR connector 440 for programming and debugging of controller 300. One suitable connector is a BM08B-SURS-TF model from JST Mfg. Co. Ltd of Osaka, Japan. The circuit also includes a light emitting diode (LED) 442 connected to controller 300 through a resistor 444 which indicates when the controller is set to debug mode. A LED 446 is connected to controller 300 through a resistor 448 and indicates when the controller is operating. A LED 450 is connected to controller 300 through a resistor 452 and indicates that power is being supplied to the system. An 8 MHz oscillator 454 provides clock signals for controller 300.

FIG. 5 depicts the inner or second surface 114 of substrate 110. In FIG. 5, camera view area 502 has an anti-reflective coating 504 deposited thereon. Anti-reflective coating 504 may extend beyond view area 502 including into the defroster deposition area radially-outward of view area 502. After anti-reflective coating 504 is deposited, a defroster coating is deposited on second surface 114 to form the lens or second surface defroster 202. The defroster 202 is deposited radially-outward from view area 502, and may comprise a transparent conductive oxide (TCO) material such as indium tin oxide. As shown in FIG. 5, the defroster coating extends about 250 degrees around the view area 502, although other defroster configurations may be used. Electrical contacts 204 and 206 are formed at opposite ends of defroster 202 by metal deposition, and electrical wires 208 and 210 (FIG. 2) are soldered to electrical contacts 204 and 206 respectively.

Figure 6:
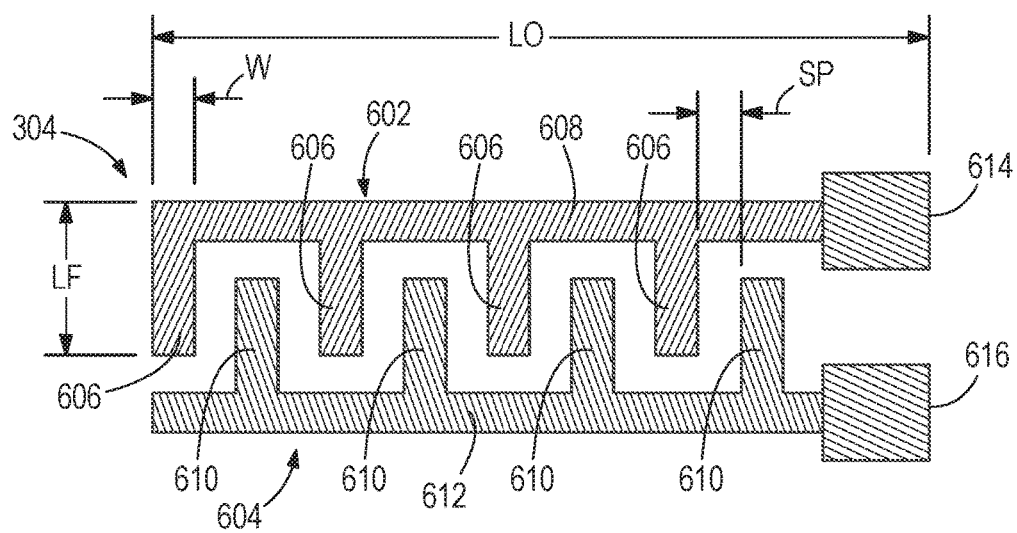
FIG. 6 depicts first and second spaced electrodes of the capacitive sensor according to the invention.

FIGS. 5 and 6 depict a capacitive sensor 202 according to an embodiment of the invention. In FIGS. 5 and 6, capacitive sensor 202 is an inter-digital sensor having a first electrode 602 and a second electrode 604 spaced from first electrode 604. First electrode 602 has a first plurality of spaced fingers 606 extending from a first base 608, and second electrode 604 has a second plurality of spaced fingers 610 extending from a second base 612. First and second electrical contacts 614 and 616 are formed by metal deposition at ends of respective first base 608 and second base 612. Wires are soldered to the electrical contacts. In the embodiment shown in FIGS. 5 and 6 and assuming a substrate 110 thickness of less than about 4.5 mm, the first and second electrodes have an overall length LO of 37 mm including their electrical contacts, and each finger has a length LF of between about 7 mm and 20 mm or greater; in the embodiment depicted in FIG. 5, the finger length LF is about 12 mm. In FIGS. 5 and 6, the fingers 606 and 610 have a width W of 2 mm, and the spacing SP between adjacent fingers from the first plurality and the second plurality is 2 mm. The size of the capacitive sensor 202 is dependent upon the thickness of the substrate 110 on which the capacitive sensor has been deposited. The thicker the substrate, the larger the capacitive sensor.

Figure 7:
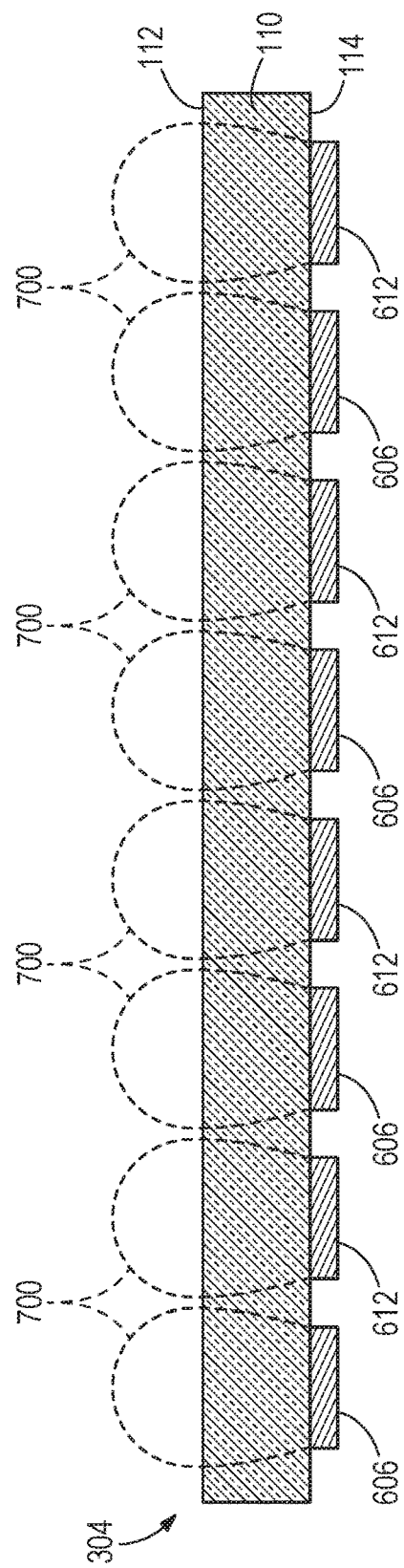
FIG. 7 is an end view of a capacitive sensor according to the invention.

FIG. 7 is an end view of capacitive sensor 304 according to an embodiment of the invention. First surface 112 of substrate 110 is exposed to moisture and debris from the environment. Capacitive sensor 304 is disposed on the opposite second surface 114 of substrate 110. Fringe fields—represented by field lines 700—of electrostatic potential emanate from capacitive sensor 304 and penetrate glass substrate 110. The magnitude of the fringe fields varies with the type of glass and environmental conditions, and also changes when a substance (e.g. water or another liquid, ice, or debris such as mud or leaves) is present on the first surface 112 of substrate 110. The fringe fields 700 and thus the overall capacitance of the capacitive sensor vary depending upon the state (i.e. liquid or solid) of the substance on first surface 112 of substrate 110, and depending upon whether there is any debris on the first surface 112. As a result, the overall capacitance of the capacitive sensor differs from the baseline capacitance for the substrate 110 as a function of the substance present on first surface 112, and these differences may be used by controller 300 to control wiper 116, lens defroster 202, wiper defroster 310, and washer 316.

The embodiments of the invention use the sensed capacitance of substrate 110 to make a determination as to which type of substance is present on substrate 1110. The capacitance is determined by the equation $$\text{Capacitance} = (\text{permittivity})(\text{area of capacitor})/(\text{distance between capacitor plates}) \quad \text{(Eq 1)}$$

Permittivity is dependent upon the nature of the material or substance. In general and for a finite, similar volume of the substance, the permittivities of selected substances which are present on a glass substrate of known surface area are mathematically related as follows:

$$\text{water} > \text{mud paste} > \text{ice} > \text{dry soil} > \text{oil} \quad \text{(Eq 2)}$$

As a result, the sensed capacitance of substrate 110 may be used to determine the nature of the substance on the substrate 110 and to take an appropriate action.

Figure 8A:
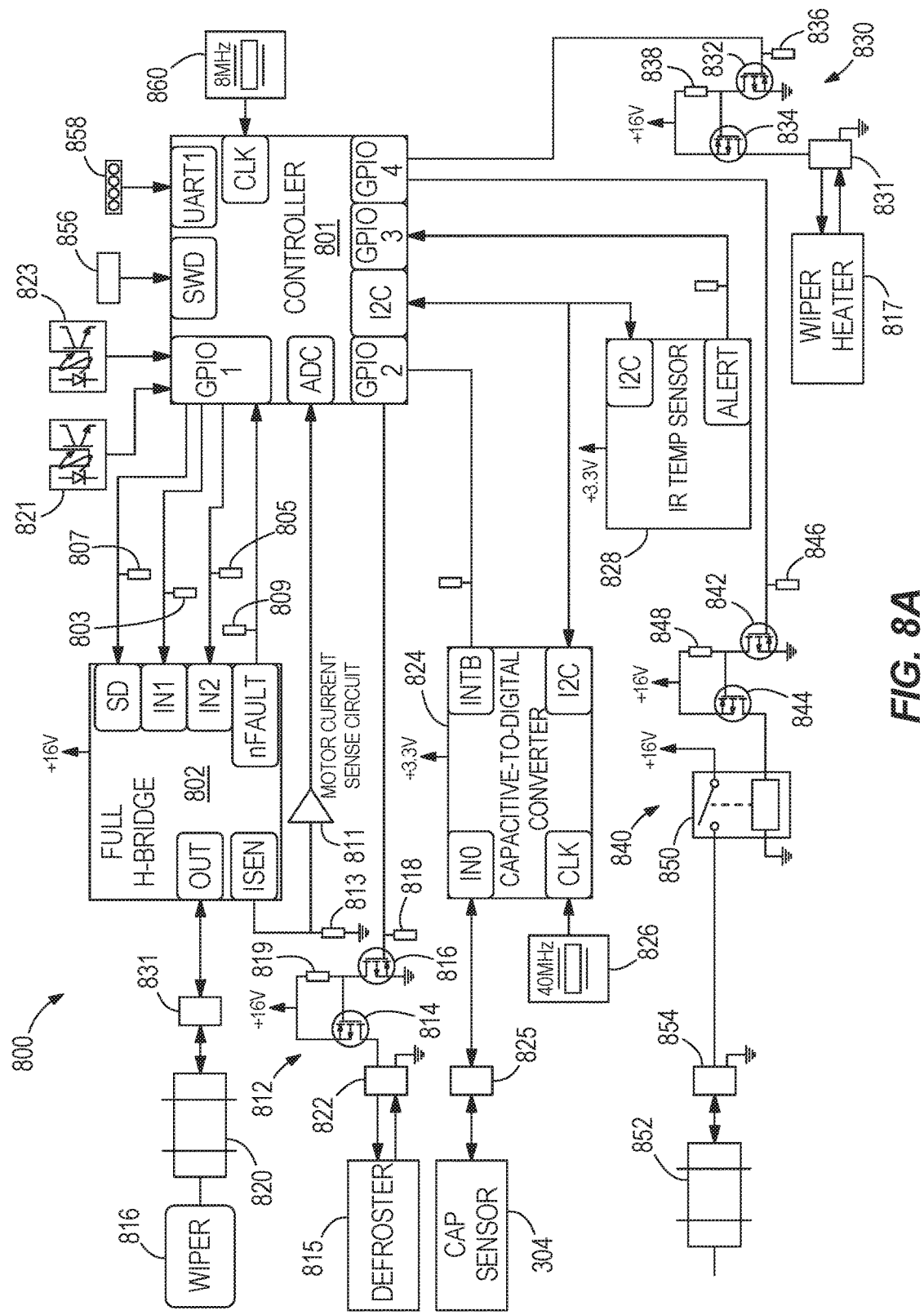
FIG. 8A is a circuit diagram of another embodiment of a camera sensor system according to the invention.

FIG. 8A is a circuit diagram relating to another embodiment of the invention. Unless otherwise indicated, the circuit in FIG. 8A functions similarly to the circuit discussed above in connection with FIG. 4A, except that in this circuit, the controller has full control of the wiper motor's direction and the controller can stop the wiper motor at any point in the wipe cycle and change its direction. In the other circuit of FIG. 4A, the wiper direction will not change until one of the phone interrupter flags is sensed by the circuit.

In FIG. 8A, circuit 800 includes a controller 801 that communicates with devices and sensors in the capacitive moisture sensor system. Controller 801 is a STM32F303 controller that is pin compatible with controller 300 in FIG. 4A except that controller 801 is an Arm-Cortex-M4 whereas controller 300 is an Arm-Cortex M3.

Controller 801 has a General Purpose Input Output GPIO1 that includes a pin array. GPIO1 is in communication with a full H-bridge 802 which in turn controls wiper motor 820. The H-bridge is preferably a Texas Instruments DRV 8872. GPIO1 includes a first pin connected to an input IN1 of H-bridge 802 through a pull-down resistor 803 and a second pin connected to input IN2 of H-bridge 802 through a pull-down resistor 805. GPIO1 also includes a third pin that can send a shutdown signal to port SD of H-bridge 802 through a pull down resistor 807 to initiate the stop, reversal or speed change of the wiper motor at any point. GPIO 1 also includes a fourth pin that can receive a fault signal from port nFault of H-bridge 802 to initial a shutoff of the H-bridge 802 and the wiper motor 820 through a pull-up resistor 809.

The H-bridge 802 also receives a signal at port ISEN indicative of the motor current as sensed by a motor current sense circuit 811 and a resistor 813. Sense circuit 811 is part of a feedback loop. Sense circuit 811 monitors the motor current to determine if a physical obstruction (e.g. a frozen wiper blade, ice build-up, or other object) is present on the camera lens surface. The output of sense circuit 811 is sent to an analog-to-digital port ADC of controller 801. The sense circuit feedback loop enables the controller 801 to protect the wiper motor 820 and to turn on or off certain components of the moisture sensing system (e.g. the wiper 816, lens defroster 815 or wiper heater 817) depending upon varying conditions.

Two photo interrupters 821 and 823 provide inputs to controller port GPIO2. Photo interrupter 821 provides a signal indicative of the wiper's park position, and photo interrupter 823 provides a signal when wiper 816 is in its extended or full angular position.

In FIG. 8, H-bridge 802 includes an output port OUT comprising two output pins OUT1 and OUT2, which are connected to wiper motor 820 through an interface 831. FIG. 8B is a truth table relating to the H-bridge motor controller of FIG. 8A.

Controller 801 has a port GPIO2 that provides control signals to a defroster switch circuit 812. Switch circuit 812 includes switches 814 and 816, pull down resistor 818 and pull-up resistor 819. Switch circuit 812 is interconnected to defroster 815 through an interface 822.

Like the circuit in FIG. 4A, circuit 801 includes a capacitive to digital converter connected between the controller and the capacitive moisture sensor. In FIG. 8A, a capacitive signal from a capacitive moisture sensor 304 is input to a capacitive to digital converter 824 through an interface 825, which in turn outputs a digital capacitive signal on bus I2C to port GPIO2 of controller 801. Controller port GPIO2 also has a pin connected to an interrupt port INTB of converter 824. A 40 MHz oscillator 826 provides a clock signal to converter 824 on converter port CLK.

In FIG. 8A, an infrared temperature sensor 828 senses the temperature of lens substrate surface 114 and provides a signal to controller 801 on bus port I2C. Temperature sensor 828 provides an excessive temperature warning sign on its ALERT port to port GPIO3 of controller 801. In response to a signal from temperature sensor 826, controller 801 outputs a control signal on port GPIO4 to a wiper heater switch circuit 830 which in turn controls wiper heater 871 through an interface 831. Wiper heater switch circuit 830 includes switches 832 and 834, a pull-up resistor 836 and a pull-down resistor 838.

Controller 801 also controls a lens washer pump 852. A pump control signal is sent via controller port GPIO4 to a pump switch circuit 840 including transistor switches 842 and 844, pull-down resistor 846, pull-up resistor 848, and relay 850. Washer pump 852 in interconnected to pump switch circuit 840 through an interface 854.

Controller 801 also has a serial port SWD which connects to a cable 856 used for programming and debugging the controller. Controller port UART1 is a universal asynchronous receiver/transmitter port used to control LEDs 858, which may include power, debug mode, and heartbeat lights like those discussed in connection with FIG. 4A. Oscillator 860 provides a 8 MHz clock signal to port CLK of controller 801.

Various features and advantages of the invention are set forth in the following claims.

What is claimed is:

1. A capacitive moisture sensor for a camera, comprising:
    a substrate having a first surface configured to being exposed to moisture, and having a second surface opposite to the first surface, the substrate including a camera view area;
    a first electrode conductively coated on the second surface of the substrate and including a conductive material, the first electrode being disposed radially outward from the camera view area;
    a second electrode disposed on the second surface of the substrate and including a conductive material, the second electrode being spaced from the first electrode and being disposed radially outward from the camera view area;
    a first electrical contact deposited on the second surface of the substrate and connected in circuit with the first electrode; and
    a second electrical contact deposited on the second surface of the substrate and connected in circuit with the second electrode.

2. The capacitive moisture sensor of claim 1, wherein
    the first electrode comprises a first plurality of fingers; and
    the second electrode comprises a second plurality of fingers spaced from the first plurality of fingers.

3. The capacitive moisture sensor of claim 2, wherein each of the fingers has a length of between 7 and 16 millimeters.

4. The capacitive moisture sensor of claim 1, further comprising:
    an anti-reflective coating deposited on the second surface of the substrate.

5. The capacitive moisture sensor of claim 1, wherein the capacitive moisture sensor further comprises:
    a defroster deposited onto the substrate radially outward from the camera view area.

6. The capacitive moisture sensor of claim 1, wherein the defroster includes at least one metal-containing layer disposed adjacent to more than one portion of the camera view area.

7. A method of forming a capacitive moisture sensor on a substrate for a camera, comprising:
    coating a surface of the substrate with a conductive material to form a first electrode of a capacitor, the first electrode being formed radially outward from a camera view area of the substrate;
    coating the surface of the substrate with a conductive material to form a second electrode of the capacitor that is spaced from the first electrode, the second electrode being formed radially outward from the camera view area of the substrate;
    depositing a first electrical contact on the surface of the substrate; and
    depositing a second electrical contact on the surface of the substrate.

8. The method of claim 7, further comprising:
    forming the first electrode such that the first electrode has a first plurality of fingers;
    and forming the second electrode such that the second electrode has a second plurality of fingers.

9. The method of claim 8, further comprising:
    depositing a conductive defroster layer on the surface of the substrate.

10. The method of claim 9, further comprising:
    depositing the metal-containing defroster layer radially-outward of the camera view area.

* * * * *